(12) United States Patent
Rodriguez

(10) Patent No.: US 10,023,913 B2
(45) Date of Patent: Jul. 17, 2018

(54) SR-BI AS A PREDICTOR OF ELEVATED HIGH DENSITY LIPOPROTEIN AND CARDIOVASCULAR DISEASE

(75) Inventor: Annabelle Rodriguez, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 222 days.

(21) Appl. No.: 12/864,809

(22) PCT Filed: Jan. 29, 2009

(86) PCT No.: PCT/US2009/032421
§ 371 (c)(1),
(2), (4) Date: Jul. 27, 2010

(87) PCT Pub. No.: WO2009/097418
PCT Pub. Date: Aug. 6, 2009

(65) Prior Publication Data
US 2010/0311073 A1   Dec. 9, 2010

Related U.S. Application Data

(60) Provisional application No. 61/062,709, filed on Jan. 29, 2008.

(51) Int. Cl.
*C12Q 1/68* (2018.01)
*C12Q 1/6883* (2018.01)

(52) U.S. Cl.
CPC ..... *C12Q 1/6883* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 6,030,778 A | 2/2000 | Acton et al. | |
| 6,316,196 B1 * | 11/2001 | Morten | 435/6.14 |
| 2003/0046718 A1 | 3/2003 | Krieger et al. | |
| 2005/0223420 A1 | 10/2005 | Krieger et al. | |

OTHER PUBLICATIONS

Hegele (Arterioscler. Thromb. Vasc. Biol.; 2002, vol. 22, pp. 1058-1061).*
Lucentini (The Scientist; 2004, vol. 24, p. 20).*
Juppner (Juppner; Bone, vol. 17; 1995, pp. 39S-40S).*
Osgood (Osgood et al; The Journal of Clinical Endocrinology & Metabolism vol. 88, pp. 2869-2879; 2003).*
Roberts (Roberts et al; Hum Hered, vol. 64, pp. 107-113, 2007).*
Acton et al; Arterioscler Thromb Vasc Biol, vol. 19, pp. 1734-1743, 1999.*
Liu et al; J. Hum. Genet. vol. 53, pp. 709-717, 2008.*
Gilbert et al; J. Hypertens. vol. 31, pp. 820-829, 2013.*
Gehrisch et al; J. Mol Med. 1999, vol. 77, pp. 728-734.*
Franciso, R.E, et al., Rev. Esp. Cardiol., vol. 59 (2):154-164 (2006) "Estrogen Regulation of the Sacvenger Receptor Class B Gene: Anti-Atherogenic or Steroidogenic, is There a Priority?".
Lopez, D. & McLean, M.P., Molecular anc Cellular Edocrinology, vol. 247: 22-33(2006).
Ritsch, A., et al., Metabolism, vol. 56: 1135-1141 (2007), Scavenger Receptor Class B Type I Polymorphisms and peripheral artherial disease.
International Search Report of International Application No. PCT/US2009/032421, dated Sep. 10, 2009.
Acton, S., et al., Arterioscler Thromb Vasc Biol. (1999) 19:1734-1743.
Acton, S., et al., The Journal of Biological Chemistry, vol. 269, No. 33, (1994) pp. 21003-21009.
Acton, S., et al., Science, vol. 271, (1996) pp. 518-520.
Calvo, D., et al., The Journal of Biological Chemistry, vol. 268, No. 25, (1993) pp. 18929-18935.
Graf, G., et al., Journal of Lipid Research (2001) vol. 42, pp. 1444-1449.
Hirano, K., et al., Circulation Research, (1995) vol. 85, pp. 108-116.
Hsu, L., et al., Arterioscler Thromb Vasc Biol. (2003) 23:1869-1874.
Ji, Y., et al., The Journal of Biological Chemistry, (1997) vol. 272, No. 34, pp. 20982-20985.
Kozarsky, K., et al., Arterioscler Thromb Vasc Biol. (2000) 20:721-727.
Le Jossec, M., et al., Molecular Biology and Evolution, (2004) vol. 21, No. 4, pp. 760-769.
Loison, C., et al., British Journal of Nutrition, (2002) 87:199-210.
Loison, C., et al., Reprod. Nutr. Dev. (2002) vol. 42, pp. 101-114.
Lundasen, T., et al., The Journal of Biological Chemistry, (2003) vol. 278, No. 44, pp. 43224-43228.
Perez-Martinez, P., et al., The Journal of Clinical Endocrinology & Metabolism, vol. 90, No. 4, pp. 2297-2300.
Rigotti, A., et al., The Journal of Biological Chemistry, (1995) vol. 270, No. 27, pp. 16221-16224.
Rigotti, A., et al., Proc. Natl. Acad. Sci. USA, (1997) vol. 94, pp. 12610-12615.
Spady, D. et al., Journal of Lipid Research, (1999) vol. 40, pp. 1384-1394.

(Continued)

*Primary Examiner* — Jehanne S Sitton
(74) *Attorney, Agent, or Firm* — Johns Hopkins Technology Ventures

(57) ABSTRACT

The present invention relates to the field of single nucleotide polymorphisms (SNPs) and uses therefore as a predictor of diseases and conditions. Specifically, the present invention provides methods and kits useful in determining whether a subject is at increased risk for developing a cardiovascular disease by screening for the presence of a SNP in the scavenger receptor class B type I (SR-BI) gene of a subject.

3 Claims, 7 Drawing Sheets

(56) References Cited

OTHER PUBLICATIONS

Stangl, H., et al., Journal of Endocrinology (2002) vol. 175, pp. 663-672.
Ueda, Y., et al., The Journal of Biological Chemistry, (1999) vol. 274, No. 11, pp. 7165-7171.

* cited by examiner $p=0.02$ $p=0.03$

Panel C: * $p<0.0007$ and ** $p<0.04$ compared to murine RAW macrophages transfected with wild-type SR-BI

* $p<0.0004$ compared to wild-type

SR-BI AS A PREDICTOR OF ELEVATED HIGH DENSITY LIPOPROTEIN AND CARDIOVASCULAR DISEASE

CROSS REFERENCE TO RELATED APPLICATIONS

This application is a 371 filing of PCT application no. PCT/US2009/032421, filed Jan. 29, 2009, which claims priority to U.S. Provisional Application Ser. No. 61/062,709, filed Jan. 29, 2008, each of which is incorporated herein by reference.

STATEMENT OF GOVERNMENTAL INTEREST

This invention was made with government support under grant no. HL075646 awarded by the National Institutes of Health. The government has certain rights in the invention.

FIELD OF THE INVENTION

The present invention relates to the field of single nucleotide polymorphisms and uses therefore as a predictor of diseases and conditions.

BACKGROUND OF THE INVENTION

Cardiovascular diseases and conditions are a major cause of morbidity and mortality throughout the world. These diseases and conditions include, but are not limited to, the various disorders of the heart and the vascular system typically referred to as myocardial infarction (heart attack), atherosclerosis, ischemic heart disease, coronary artery disease, congestive heart failure, atrial and ventricular arrhythmias, hypertensive vascular diseases, and peripheral vascular diseases.

A number of approaches are currently employed for the treatment and/or prevention of cardiovascular diseases. Pharmaceutically-based therapies include lipid lowering agents (e.g., statins), aspirin and other anti-platelet agents, and anti-hypertensive medications. Lifestyle modification also plays an important role since it is known that factors such as smoking, obesity, and a high fat diet increase the risk of myocardial infarction.

It is believed that genetic factors also contribute to the development of atherosclerosis and coronary artery disease. An individual's genetic makeup is therefore a significant determinant of the likelihood that he or she will suffer a myocardial infarction, particularly at a young age. However, while a "family history" of heart disease is a significant risk factor, many heart attack victims lack such a family history and, conversely, not all individuals with such a family history do indeed develop the disease. Thus the nature of the genetic contribution to cardiovascular disease is unclear.

There is a need in the art for methods and accompanying reagents that can be used to better assess an individual's susceptibility of developing cardiovascular disease. The need for such methods and reagents is especially acute in view of the fact that, atherosclerosis frequently remains clinically silent in its early stages and yet is often evident at post-mortem examination even among individuals in their teens and twenties.

The present invention addresses this problem by presenting methods and kits useful in identifying the presence of particular single nucleotide polymorphisms (SNPs) in the scavenger receptor class B type I (SR-BI) gene. Such SNPs place the subject at greater risk of developing elevated levels of high density lipoprotein and cardiovascular disease.

SUMMARY OF THE INVENTION

The present invention provides methods and kits for identifying subjects at risk for a particular disease or condition. In one embodiment, the condition is a change in the level of high density lipoprotein or HDL. The change may be an increase or otherwise an elevated HDL level relative to the normal or desirable level of HDL. In another embodiment, the disease is a cardiovascular disease including, but not limited to, ischemia, restenosis, congestive heart failure, and atherosclerosis.

More particularly, the methods and kits of the present invention are directed to identifying in subjects the presence of one or more allelic variants in the SR-BI gene. The allelic variant may comprise a polymorphic region of the SR-BI gene. In particular embodiments, the polymorphism may comprise one or more single nucleotide polymorphisms or SNPs. Accordingly, the present invention provides methods and kits directed to identifying the presence of one or more SNPs within the SR-BI gene of a subject.

In one embodiment, the present invention provides a method of screening for elevated risk of cardiovascular disease in a subject comprising the step of screening a biological sample from the subject for the presence of a single nucleotide polymorphism (SNP) in the SR-BI gene, wherein the presence of the SNP indicates an elevated risk of cardiovascular disease in the subject. In another embodiment, the present invention provides a method for determining whether a human subject is at increased risk for developing a cardiovascular disease comprising the step of screening a biological sample from the human subject for the presence of a SNP in the SR-BI gene, wherein the presence of the SNP indicates that the human subject is at increased risk for developing a cardiovascular disease.

The present invention also provides a method for determining whether a human subject is at increased risk for developing an elevated level of high density lipoprotein comprising the step of screening a biological sample from the human subject for the presence of a SNP in the SR-BI gene, wherein the presence of the SNP indicates that the human subject is at increased risk for developing an elevated level of high density lipoprotein.

In another aspect, the methods of the present invention may be used to determine whether a subject as an increased risk of developing a cardiovascular disease. For example, a method can comprise the step of screening a biological sample from a subject for the presence of a SNP in the SR-BI gene, wherein the presence of the SNP increases the risk of the subject developing a cardiovascular disease by at least 10% relative to a subject in which such SNP is absent from the SR-BI gene. In an alternative embodiment, the method can comprise the step of screening a biological sample from a subject for the presence of a SNP in the SR-BI gene, wherein the presence of the SNP increases the risk of the subject developing a cardiovascular disease by at least about 10% to at least about 50% relative to a subject in which such SNP is absent from the SR-BI gene.

The SNP can be selected from group consisting of rs4238001, rs2070242, rs10396208, rs5891, rs5889, rs5892, rs5888, rs2278986, rs5801571, rs838897, and G404R at Exon 10. In another embodiment, the SNP is rs4238001. In an alternative embodiment, the SNP is rs2278986. In yet another embodiment, the SNP is G404R at Exon 10.

In another embodiment of the present invention, a method can comprise the step of screening a biological sample from a subject for the presence of the rs4238001 SNP in the SR-BI wherein the presence of the rs4238001 SNP indicates that the subject is at increased risk for developing a cardiovascular disease. In yet another embodiment, the method can comprise the step of screening a biological sample from a subject for the presence of the rs2278986 SNP in the SR-BI gene, wherein the presence of the rs2278986 SNP indicates that the subject is at increased risk for developing a cardiovascular disease. Alternatively, the method can comprise the step of screening a biological sample from a subject for the presence of the G404R SNP in Exon 10 of the SR-BI gene, wherein the presence of the G404R SNP in Exon 10 indicates that the subject is at increased risk for developing a cardiovascular disease.

In a further embodiment, the cardiovascular disease is selected from the group consisting of ischemia, restenosis, congestive heart failure, and atherosclerosis. The subject may have a particular condition prior to screening. For example, a subject may have hyperalphalipoproteinemia. In another embodiment, the subject may be a female.

The present invention also provides kits for carrying out the methods disclosed herein. In one embodiment, the present invention provides a kit for screening for an elevated risk of cardiovascular disease in a subject comprising (a) material for identifying the presence of a SNP in the SR-BI gene of the subject, wherein the presence of such SNP indicates an elevated risk of cardiovascular disease in the subject; (b) suitable packaging material; and optionally (c) instructional material for use of the kit.

The present invention also provides a kit for determining whether a human subject is at increased risk for developing a cardiovascular disease comprising (a) material for identifying the presence of a SNP in the SR-BI gene of the subject, wherein the presence of such SNP indicates the human subject is at increased risk for developing a cardiovascular disease in the subject; (b) suitable packaging material; and optionally (c) instructional material for use of the kit. Alternatively, the kit may be used to determine whether a human subject is at increased risk for developing an elevated level of high density lipoprotein. The kit may comprise (a) material for identifying the presence of a SNP in the SR-BI gene of the subject, wherein the presence of such SNP indicates the human subject is at increased risk for developing an elevated level of high density lipoprotein; (b) suitable packaging material; and optionally (c) instructional material for use of the kit.

In the kits of the present invention, the material may comprise at least one nucleic acid that specifically binds to a sequence selected from the group consisting of rs4238001, rs2070242, rs10396208, rs5891, rs5889, rs5892, rs5888, rs1069261, rs2278986, rs5801571, rs838897, and G404R at Exon 10. The kits may further comprise material to process a nucleic acid-comprising biological sample.

DETAILED DESCRIPTION OF THE INVENTION

Figure 1A:
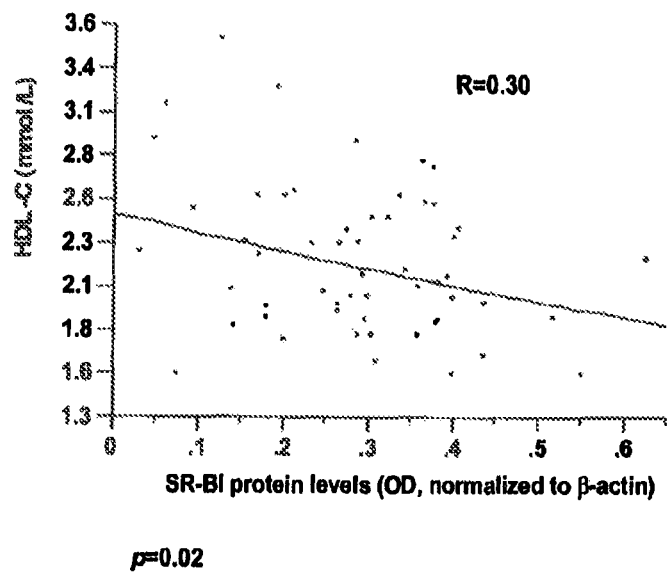
FIG. 1A. In all subjects, with hyperalphalipoproteinemia or HALP (high HDL cholesterol), HDL-C is significantly inversely associated with SR-BI protein levels. SR-BI protein levels were measured by western blotting of cell lysates isolated from monocyte-derived macrophages (MDMs) from each subject. N=55, p=0.02.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. Any and all references to a SNP by the "rs" designation, for example rs4238001 hereby incorporates the associated nucleotide sequence which is easily retrievable by known methods. Specifically, the nucleotide sequences for rs4238001, rs2070242, rs10396208, rs5891, rs5889, rs5892, rs5888, rs1069261 (see also rs27277), rs2278986, rs5801571, and rs838897 are retrievable, for example, from the NCBI SNP Database located at http://www.ncbi.nlm.nih.gov/sites/entrez. A reference to a SNP by the amino acid position change and exon/intron number (e.g., G404R at Exon 10) shall suffice to incorporate that particular sequence by reference in conjunction with the known nucleotide and amino acid sequence of the SR-BI gene which is also specifically incorporated herein by reference.

Definitions

For convenience, the meaning of certain terms and phrases employed in the specification, examples, and appended claims are provided below. The definitions are not meant to be limiting in nature and serve to provide a clearer understanding of certain aspects of the present invention.

As used herein, the term "allele" or "allelic variant" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions, and insertions of nucleotides. An allele of a gene can also be a form of a gene containing a mutation. An allelic variant may comprise one or more single nucleotide polymorphisms ("SNPs").

The term "allelic variant of a polymorphic region of an SR-BI gene" refers to a region of an SR-BI gene having one of several nucleotide sequences found in that region of the gene in a population of subjects. In certain embodiments, an "allelic variant of a polymorphic region of an SR-BI gene" may comprise a SNP within the SR-BI gene.

The term "biological sample" or "sample" means biological material isolated from a subject. The biological sample may contain any biological material suitable for detecting the desired SNP, and may comprise cellular and/or non-cellular material from the subject. For example, a biological sample may be isolated from whole blood, plasma, serum, extracellular fluid, cytosolic fluid, tissue, solubilized cellular membrane samples, cultured cells, cell culture media, physiological buffers, combinations thereof, or other biological materials known in the art.

The terms "genetic predisposition," "genetic susceptibility," and "susceptibility" all refer to the likelihood that an individual subject will develop a particular disease, condition or disorder. For example, a subject with an increased susceptibility or predisposition will be more likely than average to develop a disease or condition, while a subject with a decreased predisposition will be less likely than average to develop the disease or condition. A genetic variant is associated with an altered susceptibility or predisposition if the allele frequency of the genetic variant in a population or subpopulation with a disease, condition or disorder varies from its allele frequency in the population without the disease, condition or disorder (control population) or a control sequence (wild type).

The term "molecular structure" of a gene or a portion thereof refers to the structure as defined by the nucleotide content (including deletions, substitutions, additions of one or more nucleotides), the nucleotide sequence, the state of methylation, and/or any other modification of the gene or portion thereof.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyadenosine, deoxycytidine, deoxyguanosine, and deoxythymidine. For purposes of clarity, when referring herein to a nucleotide of a nucleic acid, which can be DNA or RNA, the terms "adenosine", "cytidine", "guanosine", and "thymidine" are used. It is understood that if the nucleic acid is RNA, a nucleotide having a uracil base is uridine.

The term "polymorphism" refers to the coexistence of more than one form of a gene or portion thereof. A portion of a gene of which there are at least two different forms, two different nucleotide sequences, is referred to as a "polymorphic region of a gene". A polymorphic region can be a single nucleotide (e.g., a SNP), the identity of which differs in different alleles. A polymorphic region can also be several nucleotides long.

A "polymorphic gene" refers to a gene having at least one polymorphic region.

The terms "protein", "polypeptide" and "peptide" are used interchangeably herein when referring to a gene product.

As used herein, the term "SR-BI" refers to scavenger receptor class B type I that has been shown to bind HDL cholesterol and mediate uptake into cells. Acton et al., 271 (5248) SCIENCE 518-520 (1996). SR-BI has also been shown to bind with high affinity to modified protein (e.g., acetylated LDL, oxidized LDL, maleylated bovine serum albumin) and native LDL (Acton et al., 269 BIOL. CHEM. 21003-21009 (1994). Further, SR-BI has been shown to bind anionic phospholipids, such as phosphatidylserine and phosphatidylinositol, but not zwitterionic phospholipids, such as phosphatidylcholine, phosphatidylethanolamine and sphingomyelin. Competition studies suggest that anionic phospholipids bind to SR-BI at a site close to or identical with the sites of native and modified LDL binding and that the interaction may involve polyvalent binding via multiple anionic phospholipid molecules. Rigotti et al., 270 J. BIOL.

CHEM. 16221-16224 (1995). SR-BI has also been shown to bind to negatively charged liposomes and apoptotic cells.

The cloning of SR-BI (sometimes referred to as "CLA-1") was first reported by Calvo and Vega in *Identification, Primary Structure, and Distribution of CIA-1, a Novel Member of the CD3/LIMPII Gene Family*, 268 (25) J. BIOL. CHEM. 18929-18935 (1993). The human SR-BI gene (also referred to as SCARB1) is at least 50 kilobase pairs long and has 12 coding exons, one non-coding exon (exon 13), and 12 introns. See, e.g., U.S. Pat. No. 6,030,778, which is incorporated herein by reference. The nucleotide sequence of the human SR-BI cDNA encodes a protein of 509 amino acids. As set forth in Calvo and Vega, supra, differential splicing of the human SR-BI gene also results in a short mRNA lacking 300 nucleotides located 126 nucleotides downstream of the initiation codon (lacking exons 2 and 3), and encodes a protein of 409 amino acids. This splice variant is rare relative to the 509 amino acid SR-BI protein.

By "increased probability" is meant at least a 10%, at least a 20%, at least a 30%, at least a 40%, at least a 50% or greater increase over a baseline probability. A baseline probability is, for example, the probability of a control subject having the indicated disease, disorder, or condition. For example, if the baseline probability is 5%, an increase of 10% means that the subject has a 5.5% probability of having or developing the condition. In particular embodiments of the present invention, the indicated condition may include a cardiovascular disease or an elevated level of high density lipoprotein.

SR-BI and Cardiovascular Disease

The present invention provides methods for identifying subjects at risk for developing cardiovascular disease. The present invention may also be used to identify subjects at risk for developing an elevated level of high density lipoprotein ("HDL"). More particularly, the present invention provides methods for identifying particular SNPs in the SR-BI gene, which SNPs result in a change in the amino acid sequence of the SR-BI protein, which in turn leads to lower amounts of the protein being made by cells. The SNPs in the SR-BI gene correlate to a risk, elevated risk, an increased probability, and/or otherwise a predisposition to develop a particular level of HDL and, in some embodiments, a cardiovascular disease including, but not limited to, ischemia, restenosis, congestive heart failure, and atherosclerosis.

In certain embodiments, the SNPs disclosed herein lead to an elevated level of HDL, which in turn, may lead to problems with cardiovascular disease. In other embodiments of the present invention, the SNPs disclosed herein may lead to infertility and other problems such as neurological diseases and hormonal diseases.

Accordingly, polymorphic changes to the SR-BI gene, which lead to an altered form and level of the SR-BI protein may be useful to identify subjects at risk, with an elevated risk, with an increased probability, and/or otherwise a predisposition for developing an elevated level and/or a cardiovascular disease. The methods and kits of the present invention are further described in more detail below.

Probes and Primers for Use According to the Present Invention

In particular embodiments of the invention, the methods and kits use probes or primers. Primers refer to nucleic acids which hybridize to a nucleic acid sequence which is adjacent to the region of interest or which covers the region of interest and is extended. A primer can be used alone in a detection method, or a primer can be used together with at least one other primer or probe in a detection method. Primers can also be used to amplify at least a portion of a nucleic acid. Probes of the invention refer to nucleic acids which hybridize to the region of interest and which are not further extended. For example, a probe is a nucleic acid which hybridizes to a polymorphic region of an SR-BI gene, and which by hybridization or absence of hybridization to the DNA of a subject will be indicative of the identity of the allelic variant of the polymorphic region of the SR-BI gene. Probes or primers can be single stranded DNA (e.g., an oligonucleotide), double stranded DNA (e.g., double stranded oligonucleotide) or RNA.

Numerous procedures for determining the nucleotide sequence of a nucleic acid, or for determining the presence of mutations in nucleic acids include a nucleic acid amplification step, which can be carried out by, e.g., polymerase chain reaction (PCR). Accordingly, in one embodiment, the invention provides primers for amplifying a portion of the SR-BI gene comprising a polymorphic region of which specific allelic variants are associated with a particular disease or condition. In a preferred embodiment, the portion of the human SR-BI gene will be amplified to, e.g., detect which allelic variant of a polymorphic region is present in the SR-BI gene of a subject. Preferred primers comprise a nucleotide sequence complementary to an SR-BI intronic sequence or a specific allelic variant of a polymorphic region and of sufficient length to selectively hybridize with an SR-BI gene. In a preferred embodiment, the primer, e.g., a substantially purified oligonucleotide, comprises a region having a nucleotide sequence which hybridizes under stringent conditions to about 6, 8, 10, or 12, preferably 25, 30, 40, 50, or 75 consecutive nucleotides of an SR-BI gene.

For example, primers comprising a nucleotide sequence of at least about 15 consecutive nucleotides, at least about 20 nucleotides or having from about 15 to about 25 are provided by the invention. Primers having a sequence of more than about 25 nucleotides are also within the scope of the invention.

Moreover, primers can be complementary to nucleotide sequences located close to each other or further apart, depending on the use of the amplified DNA. For example, primers can be chosen such that they amplify DNA fragments of at least about 10 nucleotides or as much as several kilobases. Preferably, the primers of the invention will hybridize selectively to nucleotide sequences located about 150 to about 350 nucleotides apart.

Yet other primers of the invention are nucleic acids which are capable of selectively hybridizing to an allelic variant of a polymorphic region of an SR-BI gene. Thus, such primers can be specific for any SR-BI gene sequence, provided that they have a nucleotide sequence which is capable of hybridizing to an SR-BI gene. Preferred primers are capable of specifically hybridizing to an allelic variant or SNP described in Table 4. Such primers can be used, e.g., in sequence specific oligonucleotide priming, under stringent hybridization conditions.

Preferred probes of the invention have a number of nucleotides sufficient to allow specific hybridization to the target nucleotide sequence. Where the target nucleotide sequence is present in a large fragment of DNA, such as a genomic DNA fragment of several tens or hundreds of kilobases, the size of the probe may have to be longer to provide sufficiently specific hybridization, as compared to a probe which is used to detect a target sequence which is present in a shorter fragment of DNA. For example, in some diagnostic methods, a portion of an SR-BI gene may first be amplified and thus isolated from the rest of the chromosomal DNA and then hybridized to a probe in such a situation, a shorter probe will likely provide sufficient specificity of hybridization. For example, a probe having a nucleotide sequence of about 10 nucleotides may be sufficient.

In preferred embodiments, the probe or primer further comprises a label attached thereto, which, e.g., is capable of being detected, e.g. the label group is selected from amongst radioisotopes, fluorescent compounds, enzymes, and enzyme co-factors.

In a preferred embodiment of the invention, the probe or primer is modified, such as to become more stable. Exemplary nucleic acid molecules which are modified include phosphoramidate, phosphothioate and methylphosphonate analogs of DNA. See, e.g., U.S. Pat. No. 5,176,996; U.S. Pat. No. 5,264,564; and U.S. Pat. No. 5,256,775.

The probes and primers can also be modified at the base moiety, sugar moiety, or phosphate backbone, for example, to improve stability of the molecule. The probes or primers may include other appended groups such as peptides (e.g., for targeting host cell receptors in vivo), or agents facilitating transport across the cell membrane (see, e.g., Letsinger et al., 86 PROC. NATL. ACAD. SCI. USA 6553-56 (1989); Lemaitre et al., 84 PROC. NATL. ACAD. SCI. USA 648-52 (1987); PCT Publication No. WO88/0981.0), hybridization-triggered cleavage agents (see, e.g., Krol et al., 6 BIOTECHNIQUES 958-76 (1988) or intercalating agents (see, e.g., Zon, 5 PHARM. RES. 539-49 (1988). To this end, the nucleic acid of the invention may be conjugated to another molecule, e.g., a peptide, hybridization triggered cross-linking agent, transport agent, hybridization-triggered cleavage agent, etc.

The probes and primers may comprise at least one modified base moiety which is selected from the group including but not limited to 5-fluorouracil, 5-bromouracil, 5-chlorouracil, 5-iodouracil, hypoxanthine, xanthine, 4-acetylcytidine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytidine, 5-methylcytidine, N6-adenine, 7-methylguanine, 5-methylaminomethyluracil, 5-methoxyaminomethyl-2-thiouracil, beta-D-mannosylqueosine, 5' methoxycarboxymethyluracil, 5-methoxyuracil, 2-methylthio-N-6-isopentenyladenine, uracil-5-oxyacetic acid (v), wybutoxosine, pseudouracil, queosine, 2-thiocytidine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl)uracil, (acp3)w, and 2,6-diaminopurine.

The probes and primers may also comprise at least one modified sugar moiety selected from the group including but not limited to arabinose, 2-fluoroarabinose, xylulose, and hexose.

In yet another embodiment, the probe or primer comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

Kits

The present invention provides methods for identifying the presence of single nucleotide polymorphisms in the SR-BI gene which are associated with an elevated risk of developing a particular disease or condition including, but not limited to, cardiovascular disease, neurological diseases, hormonal disorders, infertility, and an elevated level of high density lipoprotein. In certain embodiments, the present invention provides kits for conducting such methods. For example, the kit can be used to determine whether a subject is at increased risk, or has an elevated risk for, developing a cardiovascular disease including, but not limited to ischemia, restenosis, congestive heart failure, and atherosclerosis. In another embodiment, the kit may be used to determine whether a subject is at increased risk for, or has an elevated risk for developing an elevated level of HDL. The kits may be used to determine whether a subject has an increased probability of developing a particular disease or condition.

The kits of the present invention can also be used to determine if a subject who has a particular disease or condition including, but not limited to, cardiovascular disease, neurological diseases, hormonal disorders, infertility, and an elevated level of high density lipoprotein, possesses a SNP in the SR-BI gene. Such information could then be used to optimize treatment to those particular individuals.

In one embodiment, the kit comprises material for identifying the presence of a SNP in the SR-BI gene of a subject. The presence of such SNP indicates that the subject is at increased risk for developing a particular disease or condition. In a specific embodiment, the kit comprises a probe or primer which is capable of hybridizing to the SR-BI gene and thereby identifying whether the SR-BI gene contains a SNP. The kit may further comprise suitable packaging material including, but not limited to, ice, dry ice, styrofoam, foam, plastic, cellophane, shrink wrap, bubble wrap, paper, cardboard, starch peanuts, twist ties, metal clips, metal cans, drierite, glass, and rubber. The kits of the present invention may further comprise instructional material for using the kit, e.g., instructions on practicing the methods of the present invention. A kit of the present invention may further comprise instructions for use in diagnosing a subject as having, or having a predisposition, an elevated risk or otherwise an increased probability, for developing a particular disease or condition.

A person of ordinary skill in the art, utilizing known sequences and methods including those incorporated by reference herein, can design probes or primers necessary for use in the methods and kits of the present invention. Indeed, a probe or primer can be prepared according to methods well known in the art and described, e.g., in Sambrook, T. Fritsch, F. F., and Maniatis, T, (1989) Molecular Cloning: A Laboratory Manual, Cold Spring Harbor Laboratory Press, Cold Spring Harbor, N.Y. For example, discrete fragments of the DNA can be prepared and cloned using restriction enzymes. Alternatively, probes and primers can be prepared using the Polymerase Chain Reaction (PCR) using primers having an appropriate sequence.

Oligonucleotides may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al., 16 NUCL. ACIDS RES. 3209-3221 (1988), and methylphosphonate oligonucleotides can be prepared by use of controlled pore glass polymer supports (Sarin et al., 87 PROC. NATL. ACAD. SCI. USA 7448-7451 (1988).

A kit of the present invention may comprise two primers. In one embodiment, at least one primer is capable of hybridizing to an SR-BI intronic sequence, in another embodiment of the present invention, at least one primer is capable of hybridizing to an SR-BI exonic sequence. The kits of the present invention can also comprise one or more control nucleic acid or reference nucleic acids, such as nucleic acids comprising an SR-BI intronic or an exonic sequence. For example, a kit can comprise primers for amplifying a polymorphic region of an SR-BI gene (i.e., a region containing a SNP) and a control DNA corresponding to such an amplified DNA and having the nucleotide sequence of a specific allelic variant. Thus, direct comparison can be performed between the DNA amplified from a subject and the DNA having the nucleotide sequence of a specific allelic variant.

In yet another embodiment, the kits can comprise at least one reagent, buffer, or other material necessary to perform the assay. The kits can further comprise materials necessary to handle, contain, or manipulate a biological sample from a subject. For example, the kits can comprise a vial, tube, or any other container which contains one more oligonucleotides or primers which hybridize to a nucleic acid isolated from a subject, or a nucleic acid derived from a subject, e.g., an amplification product. The kits may also contain components of the amplification system, including PCR reaction materials such as buffers and a thermostable polymerase. A kit of the invention can be used in conjunction with commercially available amplification kits, e.g., from invitrogen (San Diego, Calif.), Strategene (La Jolla, Calif.), Boehringer Manheim (Indianapolis, Ind.). The kits of the present invention also can comprise positive or negative control reactions or markers, molecular weight size markers for gel electrophoresis, and the like.

Diagnostic Methods

The present invention provides methods for determining the molecular structure of at least one polymorphic region of an SR-BI gene, specific allelic variants of the polymorphic region being associated with a particular disease or condition including, but not limited to, cardiovascular disease, neurological diseases, hormonal disorders, infertility, and an elevated level of high density lipoprotein. In one embodiment, determining the molecular structure of a polymorphic region of an SR-BI gene comprises determining the identity of the allelic variant. A polymorphic region of an SR-BI gene, of which specific alleles may be associated with a particular disease or condition including cardiovascular disease and an elevated HDL level can be located in an exon, an intron, at an intron/exon border, or in the promoter of the SR-BI gene.

The invention provides methods for determining whether a subject has, or is at increased risk, of developing a particular disease or condition including cardiovascular disease and an elevated HDL level. Such disorders can be associated with an aberrant SR-BI activity, e.g., abnormal binding to a form of a lipid, or an aberrant SR-BI protein level. An aberrant SR-BI protein level can result from an aberrant transcription or post-transcriptional regulation. Thus, allelic differences in specific regions of an SR-BI gene can result in differences of SR-BI protein due to differences in regulation of expression. In particular, some of the identified polymorphisms in the human SR-BI gene may be associated with differences in the level of transcription, RNA maturation, splicing, or translation of the SR-BI gene or transcription product.

In particular embodiments, the methods of the invention can be characterized as comprising screening a biological sample from a subject for the presence of a specific allelic variant of one or more polymorphic regions of an SR-BI gene. The allelic differences can be: (i) a difference in the identity of at least one nucleotide or (ii) a difference in the number of nucleotides, which difference can be a single nucleotide or several nucleotides. The present invention also provides methods for detecting differences in SR-BI genes such as chromosomal rearrangements, e.g., chromosomal dislocation.

As described in more detail herein, methods useful in screening for the presence of a specific allelic variant of one more polymorphic regions of an SR-BI gene include, for example, DNA sequencing, hybridization techniques, PCR based assays, fluorescent dye and quenching agent-based PCR assay (Taqman PCR detection system), RFLP-based techniques, single strand conformational polymorphism (SSCP), denaturating gradient gel electrophoresis (DGGE), temperature gradient gel electrophoresis (TGGE), chemical mismatch cleavage (CMC), heteroduplex analysis based system, techniques based on mass spectroscopy, invasive cleavage assay, polymorphism ratio sequencing (PRS), microarrays, a rolling circle extension assay, HPLC-based techniques, DHPLC-based techniques, oligonucleotide extension assays (OLA), extension based assays (ARMS, (Amplification Refractory Mutation System), ALEX (Amplification Refractory Mutation Linear Extension), SBCE (Single base chain extension), a molecular beacon assay, invader (Third wave technologies), a ligase chain reaction assay, nuclease assay-based techniques, hybridization capillary array electrophoresis (CAE), pyrosequencing, protein truncation assay (PTT), immunoassays, haplotype analysis, and solid phase hybridization (dot blot, reverse dot blot, chips).

One type of screening method is allele specific hybridization using probes overlapping the polymorphic site and having about 5, 10, 20, 25, or 30 nucleotides around the polymorphic region. In one embodiment of the invention, several probes capable of hybridizing specifically to allelic variants are attached to a solid phase support, e.g., a "chip". Oligonucleotides can be bound to a solid support by a variety of processes, including lithography. Indeed, a chip can hold up to 250,000 oligonucleotides (GeneChip®, Affymetrix®). In one embodiment, a chip comprises all the allelic variants of at least one polymorphic region of an SR-BI gene. The solid phase support is then contacted with a test nucleic acid and hybridization to the specific probes is detected. Accordingly, the identity of numerous allelic variants of one or more genes can be identified in a simple hybridization experiment.

In other screening methods, it is necessary to first amplify at least a portion of an SR-BI gene prior to identifying the allelic variant. Amplification can be performed, e.g., by PCR, according to methods known in the art. In one embodiment, genomic DNA of a cell is exposed to two PCR primers and amplification for a number of cycles sufficient to produce the required amount of amplified DNA. In particular embodiments, the primers are located between 150 and 350 base pairs apart.

Alternative amplification methods include: self sustained sequence replication (Guatelli et al., 87 Proc. Natl. Acad. Sci. USA 1874.78 (1990), transcriptional amplification system (Kwok et al., 86 Proc. Natl. Acad. Sci. USA 1173-77 (1989), Q-Beta Replicase (Lizardi et al., 6 Bio/Technology 1197-1202 (1988), or any other nucleic acid amplification method, followed by the detection of the amplified molecules using techniques well known to those of skill in the art. These detection schemes are especially useful for the detection of nucleic acid molecules if such molecules are present in very low numbers.

In a further embodiment, protection from cleavage agents (such as a nuclease, hydroxylamine or osmium tetroxide and with piperidine) can be used to detect mismatched bases in RNA/RNA DNA/DNA, or RNA/DNA heteroduplexes (Myers et al. 230 (4731) Science 1242-46 (1985). In general, the technique of "mismatch cleavage" starts by providing heteroduplexes formed by hybridizing a control nucleic acid, which is optionally labeled, e.g., RNA or DNA, comprising a nucleotide sequence of an SR-BI allelic variant with a sample nucleic acid, e.g., RNA or DNA, obtained from a tissue sample. The double-stranded duplexes are treated with an agent which cleaves single-stranded regions of the duplex such as duplexes formed based on base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, e.g., Cotton et al., 85 Proc. Natl. Acad. Sci. USA 4397-4401 (1988); Saleeba et al., 217 Methods Enzymod. 286-95 (1992). In a preferred embodiment, the control or sample nucleic acid is labeled for detection.

In other embodiments, alterations in electrophoretic mobility can be used to identify the type of SR-BI allelic variant. For example, single strand conformation polymorphism (SSCP) may be used to detect differences in electrophoretic mobility between mutant and wild type nucleic acids. See Orita et al. 86 Proc Natl. Acad. Sci, USA 2766-70 (1989), see also Cotton 285 Mut. Res. 125-144 (1993); and Hayashi, 9 Genet. Anal. Tech. Appl. 73-79 (1992). Single-stranded DNA fragments of sample and control nucleic acids are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In another embodiment, the method utilizes heteroduplex analysis to separate double stranded heteroduplex molecules on the basis of changes in electrophoretic mobility. See Keen et al. 7 Trends Genet. 5-10 (1991).

In yet another embodiment, the identity of an allelic variant of a polymorphic SR-BI region can be obtained by analyzing the movement of a nucleic acid comprising the polymorphic region in polyacrylamide gels containing a gradient of denaturant is assayed using denaturing gradient gel electrophoresis (DGGE). Myers et al., 313 Nature 495-498 (1985). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA. Rosenbaum and Reissner, 265 Biophys. Chem. 1275 (1987).

Examples of techniques for detecting differences of at least one nucleotide between 2 nucleic acids include, but are not limited to, selective oligonucleotide hybridization, selective amplification, or selective primer extension. For example, oligonucleotide probes may be prepared in which the known polymorphic nucleotide is placed centrally (allele-specific probes) and then hybridized to target DNA under conditions which permit hybridization only if a perfect match is found. Saiki et al., 324 Nature 163-166 (1986); Saiki et al., 86 Proc. Natl. Acad. Sci. USA 6230-34 (1989); and Wallace et al., 6 Nucl. Acids Res. 3543-57 (1979). Such allele specific oligonucleotide hybridization techniques may be used for the simultaneous detection of several nucleotide changes in different polymorphic regions of SR-BI. For example, oligonucleotides having nucleotide sequences of specific allelic variants are attached to a hybridizing membrane and this membrane is then hybridized with labeled sample nucleic acid. Analysis of the hybridization signal will then reveal the identity of the nucleotides of the sample nucleic acid.

Alternatively, allele specific amplification technology which depends on selective PCR amplification may be used in conjunction with the instant invention. Oligonucleotides used as primers for specific amplification may carry the allelic variant of interest in the center of the molecule (so that amplification depends on differential hybridization) (Gibbs et al., 17 Nucl. Acids Res. 2437-48 (1989) or at the extreme 3' end of one primer where, under appropriate conditions, mismatch can prevent, or reduce polymerase extension (Prossner, 11 Tibtech 238-46 (1993); Newton et al., 17 Nucl. Acids Res. 2503-16 (1989). This technique is also termed "PROBE" for Probe Oligo Base Extension. In addition it may be desirable to introduce a novel restriction site in the region of the mutation to create cleavage-based detection. Gasparini et al. 6 Mol. Cell. Probes 1-7 (1992).

In another embodiment, identification of the allelic variant is carried out using an oligonucleotide ligation assay (OLA), as described, e.g., in U.S. Pat. No. 4,998,617 and in Landegren et al., 241 Science 1077-80 (1988). The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA. Nickerson et al., 87 Proc. Natl. Acad. Sci. USA 8923-27 (1990). In this method, PCR is used to achieve the exponential amplification of target DNA, which is then detected using OLA.

Several techniques based on this OLA method have been developed and can be used to detect specific allelic variants of a polymorphic region of an SR-BI gene. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA, OLA combined with PCR permits typing of two alleles in a single microtiter well. See Tobe et al. 24 Nucl. Acids Res. 3728-32 (1996). By marking each of the allele-specific primers with a unique hapten, i.e., digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

In addition to the methods recited above, the present invention further provides methods for detecting single nucleotide polymorphisms (SNPs) in an SR-BI gene. Because SNPs constitute sites of variation flanked by regions of invariant sequence, their analysis requires no more than the determination of the identity of the single nucleotide present at the site of variation and it is unnecessary to determine a complete gene sequence for each patient Several methods have been developed to facilitate the analysis of such single nucleotide polymorphisms.

In one embodiment, the single base polymorphism can be detected by using a specialized exonuclease-resistant nucleotide, as disclosed, e.g., in U.S. Pat. No. 4,656,127. According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Because the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the present invention, a solution based method is used for determining the identity of the nucleotide of a polymorphic site. PCT Publication No. WO91/02087). A primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method known as Genetic Bit Analysis or GBA is described by Goelet, P. et al. (PCT Publication No. WO92/15712). The method uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method described in PCT Publication No. WO91/02087, this method is preferably a heterogeneous phase assay, in which the primer or the target molecule is immobilized to a solid phase.

Several primer-guided nucleotide incorporation procedures for assaying polymorphic sites in DNA have been described. See generally, Komher et al., 17 Nucl. Acids. Res. 7779-84 (1989); Sokolov, 18 Nucl. Acids Res. 3671 (1990); Syvanen et al., 8 Genomics 684-92 (1990), Kuppuswamy et al., 88 Proc. Natl. Acad. Sci. USA 1143-47 (1991); Prezant et al., 1 Hum. Mutat. 159-64 (1992); Ugozzoli et al., 9 GATA 107-12. (1992); Nyren et al., 208 Anal. Biochem. 171-75 (1993). These methods differ from GBA in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run. See also Syvanen et al., 52 Amer. J. Hum. Genet. 46-59 (1993).

If a polymorphic region is located in an exon, either in a coding or non-coding region of the gene, the identity of the allelic variant can be determined by determining the molecular structure of the mRNA, pre-mRNA, or cDNA. The molecular structure can be determined using any of the above described methods for determining the molecular structure of the genomic DNA, e.g., sequencing and SSCP.

The methods described herein may be performed, for example, by utilizing pre-packaged diagnostic kits, such as those described above, comprising at least one probe or primer nucleic acid described herein, which may be conveniently used, e.g., to determine whether a subject has or is at increased risk of developing a disease associated with a specific SR-BI allelic variant.

The methods of the present invention, including methods for identifying the presence of an allelic variant or SNP in the SR-BI gene of a subject may be combined with other information or parameters using the methods well known in the art to aid in the identification of subject with deficiency in the SR-BI protein. Such additional information or parameters may include, but is not limited to, lipid levels, hormone levels, adipokines, nitric oxide metabolites, serum inflammatory markers, and/or measurements of subclinical atherosclerosis.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

Materials and Methods:
Study Subjects
Adult men and women between the ages of 18-80 years were recruited from the greater Baltimore, Md. area. Subjects presented to The Johns Hopkins Bayview Medical Center General Clinical Research Center in the fasting state on 2 separate visits held 2 weeks apart, and the mean fasting plasma HDL-C had to be 1.55 mmol/L (60 mg/dl) for inclusion in this study. Subjects were not taking cholesterol medications (statins, fibrates or niacin) and had normal liver, renal and thyroid function tests. Study subjects donated 150 ml of blood following an overnight fast for the purposes of isolating plasma, serum, lipoproteins, circulating monocytes for in vitro macrophage differentiation and genomic DNA for sequencing of the SR-BI gene. Fasting lipid profiles were measured by routine commercial assays with the LDL-C calculated using the Friedewald equation. Friedewald et al., 18 CLIN. CHEM. 499-502 (1972). Hepatic lipase (HL), endothelial lipase (EL), lipoprotein lipase (LPL) phospholipase activities were measured from post heparin plasma according to the methods of McCoy et al. using a glycerol-stabilized emulsion that contained radiolabeled phospholipid and cholesteryl oleate as the neutral lipid core. See McCoy et al., 43 J. LIPID RES. 921-29. (2002). EL, HL and LPL triglyceride lipase activity was measured using a glycerol-stabilized emulsion of triolein and egg phosphatidylcholine containing glycerol-tri[9,10(n)-$^3$H]oleate. Cholesteryl ester transfer protein (CETP) and lecithin cholesteryl acyltransferase (LCAT) activities were measured by an enzymatic method as described previously. Fielding et al., 71 J. CLIN. INVEST. 449-60 (1983). The principle of this method is that the increased cholesteryl ester (CE) in plasma incubated in vitro as a result of LCAT activity is associated with an equivalent molar decrease in free cholesterol (FC). The rate of CETP-mediated transfer of CE from HDL to VLDL is then the difference between the rate of decrease in FC in whole plasma, and the rate of increase of CE in HDL, as a function of time. Study subjects provided written consent and the protocol was approved by The Johns Hopkins institutional Review Board.

The characteristics of the study population subjects are presented in Table 1A (all subjects, male and female) and Table 1B (stratified by gender). As noted below and in the figures, the data from the study is presented as "all subjects" meaning the male and female subjects and as "all females" meaning the data was reviewed in the context of females only.

Cell Culture

Peripheral blood mononuclear cells were isolated from buffy coats derived from the blood by Ficoll density gradient as described previously. Rodriguez et al., 19 ARTERIOSCLER. THROMB. VASC. ELIOT 2199-2206 (1999). After centrifugation at 2000 g for 20 minutes at 10° C. the lymphocytes were harvested from the Ficoll-plasma interface. Cells were then plated in RPMI medium containing 20% human serum and monocyte-derived macrophages (MDMs) were cultured by adherence to the tissue culture plates. After one day, non-adherent cells were removed and the monolayer washed four times with 10% human serum. Cells were then incubated with fresh 20% human serum for a total of 10-14 days.

Lipoprotein Analysis

Approximately one ml of plasma was frozen at −80° C. and then sent on dry ice, to Liposcience (Raleigh, N.C.) for lipid profile and subfraction analysis. HDL was isolated by subjecting plasma aliquots to fast protein liquid chromatography (GE HealthSciences). The HDL fractions were pooled and then an aliquot was subjected to SDS-PAGE analysis for identification of apoA-I Protein was measured by the BCA™ protein assay kit from Pierce Labs.

HDL Radiolabeling

HDL isolated from the study subjects was radiolabeled with [1,2-$^3$H]cholesteryl oleyl ether. Faust et al., 252 J. BIOL. CHEM. 4861-4871 (1977). In brief, 50 µCi of [1 α 2 α (n-$^3$H]cholesteryl oleyl ether (Amersham, Inc.) was dried under $N_2$ and then redissolved in 100 µl of dimethylsulfoxide, HDL (1 mg protein) was then added to the solution and allowed to incubate for 2 h at 40° C. At the end of the incubation period, the HDL preparations were dialyzed in 0.15M NaCl, 0.3 mM EDTA for 4 exchanges (4 L each) at 4° C. It was previously shown that the biochemical characteristics of radiolabeled HDL (electrophoretic pattern and lipid content) were similar to control, unlabeled HDL. Friedewald et al., 18 CLIN. CHEM. 499-502 (1972).

Cholesteryl Ester Uptake

MDMs from the study subjects were incubated with HDL (50 pg protein/ml) radiolabeled with [$^3$H]cholesteryl oleyl ether for 24 h. At the end of the incubation period, the medium was collected and centrifuged at 1500 rpm for 10 minutes to pellet nonadherent cells. Cellular lipids were extracted with hexane:isopropanol (3:2,v/v) (Hara et al., 90 ANAL. BIOCHEM. 420-26 (1978)), the fractions were dried under N2 and then subsequently redissolved in 1 ml of hexane. An aliquot of the medium and the cell lipid extract was counted for the presence of [$^3$H]cholesterol using liquid scintillation spectroscopy, and the selective CE uptake from HDL was calculated as (cellular [$^3$H]cholesteryl oleyl ether/[medium [$^3$H]cholesteryl oleyl ether+cellular [$^3$H]cholesteryl oleyl ether])×100%. The apoA-I moieties were not radiolabeled with $^{125}$I as there was not sufficient time between isolation of HDL and monocyte-macrophage culture to perform radioiodine labeling of HDL from each donor. Nonetheless, the method of CE uptake accurately measures a major aspect of SR-BI function, given the fact that uptake of $^{125}$I-apoA-I is negligible in SR-BI over-expressing cells. See Acton et al., 19 ARTERIOSCLER THROMB. VASC. BIOL. 1734-1743 (1999).

Western Blotting

Total cell lysates from MDMs were prepared using 5% SDS, 50 mM Tris-CI, pH 7.6 buffer in the presence of protease inhibitor cocktail (1:100) and phenylmethylsulfonylfluoride (1 mg/ml) (both from Sigma). Aliquots of the lysates (8 µg protein/lane) were subjected to SDS-PAGE in 4-10% gradient gels (BioRad Laboratories) and then transferred onto polyvinylidene fluoride membranes overnight at 4° C. Blots were blocked with 5% milk for 1 h, incubated with polyclonal anti-SR-BI (Novus) (1:1000) at 37° C. for 1 h, rinsed three times with TBS-0.1% Tween plus 5% milk, reacted with anti-rabbit HR-peroxidase labeled IgG at room temperature for an additional hour, and then rinsed three more times With TBS-0.1% Tween. Bands were visualized using an Amersham ECL™ chemiluminescence kit (GE Healthcare), quantitated by densitometric scanning and normalized to β-actin expression. Western analysis was performed at least three times for the lysates from each subject.

Real Time PCR Assay

RNA was extracted from MDMs using Trizol® (Invitrogen). After cell lysis and sample preparation the RNA was obtained by phenol extraction as Indicated in the protocol. Extracted RNAs were quantified spectrophotometrically, and stored at −80° C. until reverse transcribed. Reverse Transcriptase: Total RNA (2 µg) was reverse transcribed using the Retroscript Kit (Applied Biosystems), containing the random decamers, and moloney murine leukemia virus reverse transcriptase. Complementary DNA was synthesized at 50° C. for 1 hr. Primers for human 18S and SR-BI were designed using the Primer Express Software. Quantification by Fluorescence Real Time PCR: The Real Time PCR reaction was conducted using the 7300 RT-PCR instrument and the 7300 SDS 1.3.1 software using the following program:

50° C. for 2 min, initial denaturation for 10 min at 95° C., followed by 40 cycles of denaturing for 15 sec at 95° C., annealing for 1 min at 60° C. The reaction was performed using 12.5 µl of 2× Custom Taqman SNP Master Mix (Applied Biosystem), 1.25 µl 20× Assay mix (SR-BI primers and probes) and 1.5 ng of cDNA to a 25 µl total reaction volume. To confirm accuracy of real-time PCR the assay was run in triplicates for the target and the endogenous control. SR-BI mRNA expression was quantified using the relative quantification method (delta Ct).

Transient Transfection of COS-7 Cells

COS-7 cells were grown in 175 cm$^2$ and maintained in DMEM with 10% heat-inactivated fetal bovine serum (PBS), 100 units/ml penicillin, 100 µg/ml streptomycin at 37° C. in 95% air/5% $CO_2$. One day prior to the transfection of 150 ng pSG5-wild-type or G2S-SR-BI and 100 ng pSV-βgal using FuGENE6 reagent Costar 6-well plates were seeded with 5×10$^5$ cells per well. The total amount of transfected DNA was increased to 1 µg using pSG5 empty vector. Transfection efficiency was determined by measuring β-galactosidase expression. Twenty four hours after transfection, the cells were rinsed once with PBS and cells lysates collected to determine cellular SR-BI protein expression by western blotting and visualized bands were normalized to β-actin expression.

SR-BI Sequencing

The entire coding DNA (exons 1-12), the immediately adjacent exon-intron junctions, 1 kB upstream putative promoter, 3'- and 5'-UTR regions were characterized by direct sequencing in both directions of PCR products. Fourteen pairs of primers were synthesized in order to amplify each of the exonic regions and intronic borders of the human SR-BI gene. Sequence comparisons were determined using the Sequencher Program v.4.0 (Gene Code).

Statistics

The distribution profile was determined for each variable ascertained, and values that did not exhibit a normal distribution were log-transformed. To evaluate the association of SR-BI protein levels with quantitative traits, stepwise multiple regression analyses were performed with adjustment for a number of covariates. JMP Start Statistics, Third Edition software, SAS Institute Inc. (Cary, N.C.) was used to perform the statistical analyses and p-values≤0.05 were considered significant. Threshold significance values for selection and retention of covariates in the stepwise selection procedure were 0.25 and 0.10, respectively.

Example 1

The characteristics of the study population are shown in Tables 1A and 1B. The majority of the participants were women, with a mean age of 57.2±10.9 years for this subgroup. Nine women indicated a history of hormone therapy (HT) use, but only three women were current users.

Figure 1B:
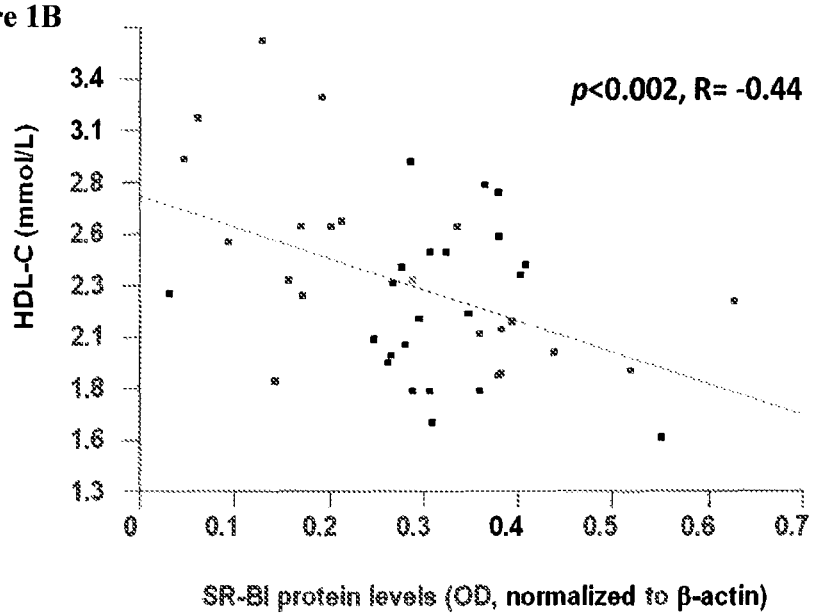
FIG. 1B. In female subjects, HDL-C also is significantly inversely associated with SR-BI protein levels. N=43, p=0.002.

The primary goal was to determine the relationship between tissue expression of SR-BI protein and HDL-C levels. The rationale for isolating MDMs from each subject was that this tissue is readily accessible—in contrast to other tissues highly expressing SR-BI such as liver, adrenals and gonads—and has been shown to express SR-BI protein. See Rodriguez et al., 100 CIRCULATION SUPPL. 538 (1999); and Hirano et al., 85 CIRC. RES. 108-116 (1999). SR-BI protein levels were found to be normally distributed, whereas SR-BI mRNA levels were not normally distributed (data not shown). As shown in FIG. 1A, in all subjects, SR-BI protein levels were inversely associated with HDL-C levels (p=0.02, r=−0.30, Pearson's correlation with outliers excluded based on values above and below the 95th and $5^{th}$ percentile [n=4]). As shown in FIG. 1B, in female subject, SR-BI protein levels were inversely associated with HDL-C levels (p=0.002, r=−0.44, Pearson's correlation with outliers excluded based on values above and below the $95^{th}$ and $5^{th}$ percentile [n=4]).

In the population of HALP subjects, there was association between HDL-C levels and CETP, HL, EL, LPL or LCAT activities (data not shown). In all subjects, when SR-BI protein levels were stratified by percentile, with low expression defined as below the $25^{th}$ percentile and high expression defined as above the $75^{th}$ percentile, HDL-C levels were significantly higher in subjects with low SR-BI protein expression (2.45±0.11 mmol/L) (94.5±4.4 mg/dl) compared with subjects with high SR-BI expression (1.97±0.13 mmol/L) (76.2±4.9 mg/di) (p=0.03, Tukey-Kramer, n=55) (data not shown). An association between SR-BI protein and LDL-C or IDL levels was not observed (data not shown).

In female subjects, when SR-BI protein levels were stratified by percentile, with low expression defined as below the 25th percentile and high expression defined as above the 75th percentile, HDL-C levels were significantly higher in subjects with low SR-BI protein expression (2.68±0.13 mmol/L) (103.5±5.0 mg/dl) compared with subjects with high SR-BI expression (2.21±0.10 mmol/L) (85.3±3.7 mg/dl) (p=0.01, Tukey-Kramer, n=43) (data not shown). An association between SR-BI protein and LDL-C or IDL levels was not observed, nor was there an association between SR-BI protein and any of the apolipoprotein measurements (data not shown).

Mice completely deficient in SR-BI have significantly higher HDL-C levels, with the HDL particles also being much larger in size. See Rigotti et al., 94 PROC NATL. ACAD. SCI. USA 12610-12615 (1997). Thus far, no humans have been identified that are completely deficient in SR-BI protein. It is hypothesized that the probability of identifying subjects deficient in SR-BI would be greatest in those subjects with HALP. As was shown in FIG. 1A, there was a significant inverse relationship between tissue expression of SR-BI and HDL-C levels. While intra-individual variation in SR-BI protein levels could not be assessed, the results from the HALP population nonetheless demonstrated a significant relationship between SR-BI protein level in macrophages and plasma HDL-C. MDMs were selected because this tissue is readily accessible and has been shown to express SR-BI protein. See Rodriguez et al., 100 CIRCULATION SUPPL. 538 (1999); and Hirano et al., 85 CIRC. RES. 108-116 (1999). Given these positive findings, it is likely that in the HALP population utilized herein, the MDMs are representative of the significant association between tissue SR-BI protein and HDL-C.

Example 2

Figure 2A:
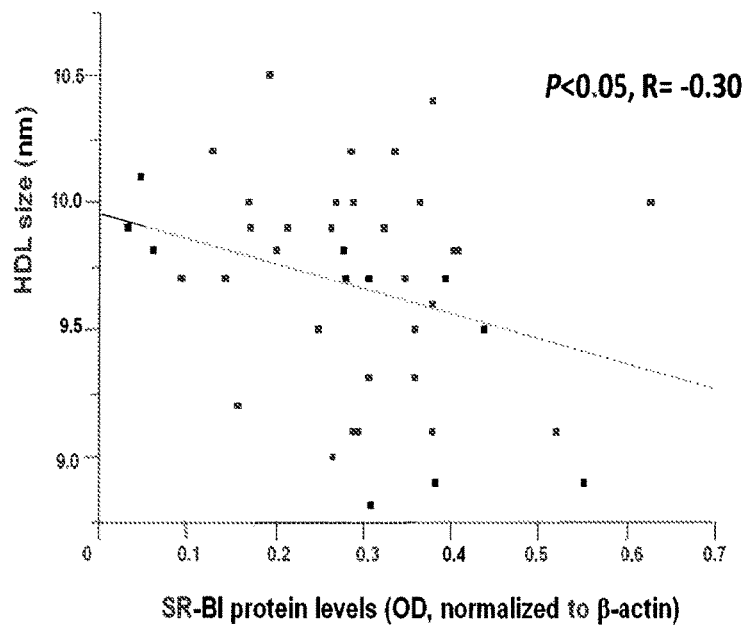
FIG. 2A. In all subjects, HDL particle size is inversely associated with SR-BI protein levels. HDL particle size was determined by NMR spectroscopy. N×54, p×0.03.
Figure 2B:
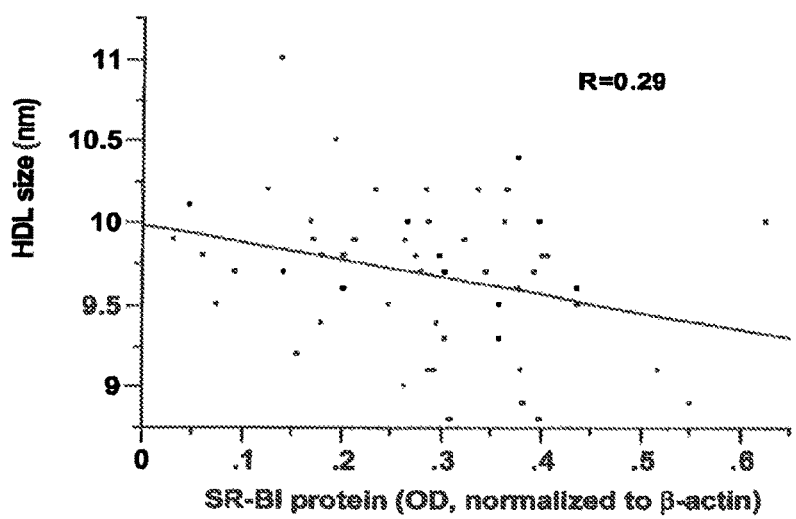
FIG. 2B. In female subjects, HDL particle size also is inversely associated with SR-BI protein levels. N=42, p<0.05.

The relationship between SR-BI protein levels and HDL size as measured by NMR spectroscopy was next determined. As shown in FIG. 2A, in all subjects, HDL particle size was inversely correlated with SR-BI protein level (p=0.03, r=−0.29, n=54). As shown in FIG. 2B, in female subjects, HDL particle size was inversely correlated with SR-BI protein level (p=0.05, r=−0.30, n=42). An association between SR-BI protein levels and VLDL particle number or size, or LDL particle number or size was not observed (data not shown).

Example 3

Figure 3A:
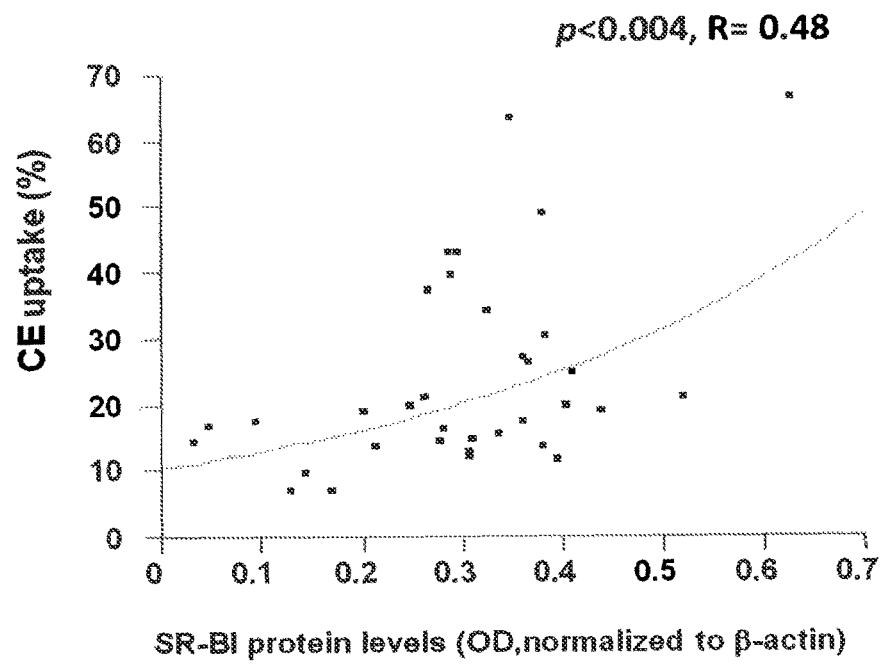
FIG. 3A. In all subjects, CE uptake from HDL is positively associated with SR-BI protein levels. HDL isolated from each study subject was radiolabeled with [1,2-$^3$H] cholesteryl oleyl ether (COE), and then incubated with each donor's respective MDMs. N=42, p=0.01.

The uptake of [3H]cholesteryl-oleyl ether mediated by HDL in MDMs isolated from the study subjects was measured. The results in FIG. 3A for male and female subjects showed that the percent CE uptake mediated by HDL was significantly associated with SR-BI protein levels (p=0.01, r=0.38, n=42). The results in FIG. 3B for female subjects showed that the percent CE uptake mediated by HDL was also significantly associated with SR-BI protein levels (p=0.004, r=0.48, n=34).

It has been shown that a significant inverse relationship between SR-BI protein levels and HDL size, which is in agreement with the findings observed in SR-BI knockout mice. See Rigotti et al., 94 PROC NATL. ACAD. SCI. USA 12610-12615 (1997). The results in FIG. 3A for male and female subjects demonstrated a positive association between SR-BI protein levels and CE uptake from HDL. Such findings are in agreement with data derived from others using in-vitro and animal models that showed the inverse relationship between SR-BI protein level, HDL size and CE uptake. See Jian et al., 273 J. BIOL. CHEM. 5599-5606 (1998); Ji et al., 272 J. BIOL. CHEM. 20982-20985 (1997); Ueda et al., 274 J. BIOL. CHEM. 7165-7171 (1999); and Kozarsky et al., 20 ARTERIOSCLER THROMB. VASC. BIOL. 721-27 (2000).

Figure 3B:
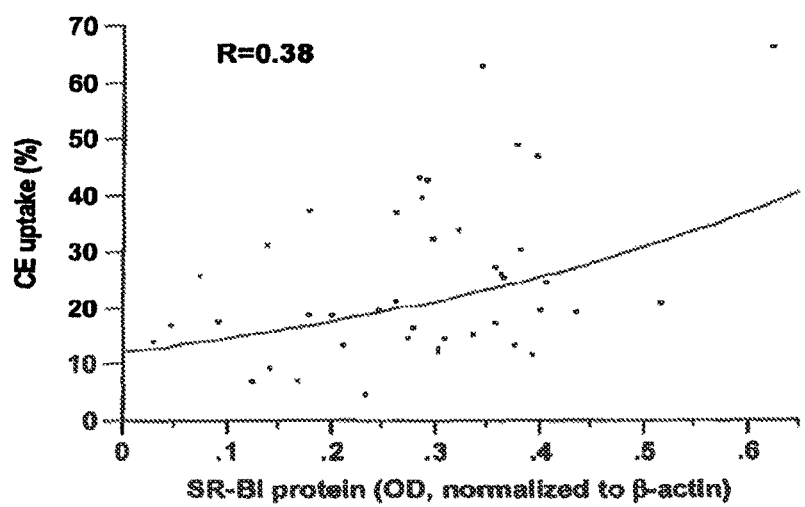
FIG. 3B. In female subjects, CE uptake from HDL also is positively associated with SR-BI protein levels. N=34, p=0.004.

The results in FIG. 3B for female subjects also showed a positive association between SR-BI protein levels and CE uptake from HDL. Selective CE uptake assays were not performed due to logistical problems in radiolabeling each donor's HDL with $^{125}I$ prior to incubation with each donor's MDMs. However, because no association between SR-BI protein levels and any of the plasma apolipoproteins was observed, this suggested that the findings were consistent with previous observations that the major function of SR-BI is to mediate the uptake of CE, and not the apolipoprotein moieties of HDL. See Rigotti et al., 271 SCIENCE 518-20

(1996). It should be noted that the results presented herein are not from subjects completely deficient in SR-BI protein, and that the primary analysis was confined to women with HALP. Moreover, while the relationship between SR-BI and CE uptake was significant, the results did not suggest that SR-BI was the only factor influencing CE uptake in human macrophages.

Example 4

Having observed that SR-BI protein levels were associated with HDL-C levels, it was next determined whether SR-BI protein was an independent predictor of HDL-C. The additional covariates of age, gender, BMI, smoking, alcohol use, exercise, HT, triglycerides (TG), hemoglobin $A_{1c}$, fish oil use and SR-BI protein levels were considered, which together explained 49% of the variance in HDL-C levels (model p=0.0001). In a multiple regression analysis, SR-BI remained a significant predictor of HDL-C levels (p=0.01) (Table 2A, all subjects). Gender (p=0.001), hemoglobin $A_1c$ (p=0.04), TG levels (p=0.007), and fish oil use (p=0.008) were also significant independent predictors of HDL-C levels.

The additional covariates of age, BMI, smoking, alcohol use, exercise, HT, triglycerides (TG), hemoglobin $A_{1C}$, fish oil use and SR-BI protein levels were also considered in female subjects, which together explained 55% of the variance in HDL-C levels (model p=0.001), in a stepwise multiple regression analysis, SR-BI remained a significant predictor of HDL-C levels (p=0.01) (Table 2B, female subjects). Triglyceride levels (p=0.01), exercise (p=0.03), and fish oil use (p=0.01) were also significant independent predictors of HDL-C levels in this HALP population.

The variables that were independent predictors of SR-BI protein levels were next determined. The covariates of gender, BMI, HT use, ethnicity, aspirin use, CETP and LCAT activities were considered, which together explained 23% of the variance in SR-BI protein levels (model p=0.01). In a multiple regression analysis, BMI (p=0.009), gender (p=0.05), and ethnicity (p=0.03) remained as significant independent predictors of SR-BI protein levels. No interactions between these variables on SR-BI protein levels were observed (data not shown).

Significant influences on SR-BI protein expression were evaluated, and it was discovered that BMI, gender, and ethnicity were independent predictors of SR-BI protein levels. With regards to the relationship of BMI and SR-BI, Acton et al. (19 ARTERIOSCLER. THROMB. VASC. BIOL. 1734-1.743 (1999)) had earlier observed that certain SR-BI SNPs were significantly associated with BMI. Moreover, Perez-Martinez et al. (90 J. CLIN. ENDOCRINOL. METAB. 2297-2300 (2005)) examined the effect of dietary fat content on lipid levels in subjects with SR-BI exon 1 SNP and reported that subjects expressing the minor allele in exon 1 had significantly higher LDL-C levels. This suggests the possibility that dietary fat might also have an important affect on SR-BI expression. In vitro studies have also shown a significant influence of fatty acids on SR-BI expression. See Spady et al., 40 J. LIPID RES. 1384-1394 (1999); Loison et al., 87 BR. J. NUTRI. 199-210 (2002); and Loison et al., 42 REPROD. NUTR. DEV. 101-14 (2002). Alternatively, adipokines such as leptin have been shown to increase hepatic SR-BI expression. Lundasen et al., 278 J. BIOL. CHEM. 43224-43228 (2003). In animals estrogen has been shown to regulate the expression of SR-Bi and its isoform SR-BII. See Graf et al., 42. J. LIPID. RES. 1444-1449 (2001); and Stangl et al., 175 J. ENDOCRINOL. 663-72. (2002). In humans, we were the first to report a significant association between low SR-BI RNA levels in granulose cells and low plasma estuarial levels in infertile women undergoing in vitro fertilization. Velasco et al., 85 FERT. STERIL. 1391-1397 (2006). There have been reports examining SR-BI genotype frequencies in different ethnic groups (Le Jossec et al., 21 MOL. BIOL. EVOL. 760-69 (2004)), but it is likely that the effect of ethnicity on SR-BI protein expression has not been previously reported. As was true with previous studies examining SR-BI genotypes on lipids, the vast majority of our study subjects were Caucasians.

Example 5

The prevalence of SR-BI (also referred to as SCARB1) gene variants were examined by directly sequencing the coding regions, intron-exon junctions, the 5'- and 3'-UTR regions, and 1 kB upstream of the initiation start site. The results in Table 4 are synonymous and nonsynonymous coding SNPs as well as noncoding SNPs found in SR-BI with a frequency greater than 10%. Five HALP subjects with a previously reported nonsynonymous SNP that encodes a change from glycine to serine in the second amino acid of the SR-BI protein (rs4238001 or G2S) were identified. Two subjects with a nonsynonymous SNP in exon 3 were identified. This SNP encodes a change from valine to isoleucine at amino acid 135 (V135I). A novel nonsynonymous SNP in exon 10 (Gly→Arg, G404R) was also identified in one subject with SR-BI protein levels below the $25^{th}$ percentile. In none of the HALP subjects were identified the 11-base pair deletion within the SR-BI promoter described by Hsu et al. (23 ARTERIOSCLER. THROMB. VASC. BIOL. 1869-1874 (2003)). In addition, none of the subjects with SR-BI protein levels above the $75^{th}$ percentile were carriers for any of the nonsynonymous SNPs identified in subjects with the lowest SRB1 protein levels.

Figure 4A:
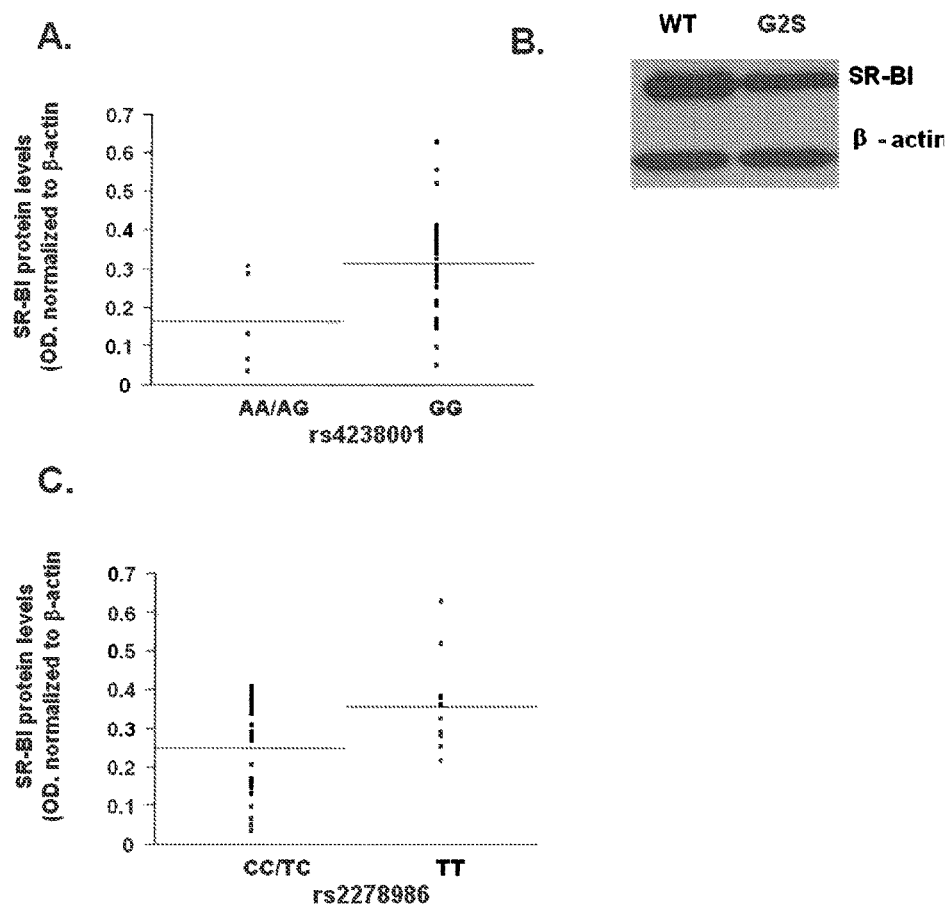
FIG. 4A. In all subjects, the association of macrophage SR-BI protein levels with the rs4238001 and rs2278986 SNPs. Panel A: SR-BI protein levels were significantly lower in carriers of the A allele (AA/AG) fix the rs4238001 SNP compared with non-carriers (GG) (p=0.007, r=0.36, n=55). Panel B: COS-7 cells transiently transfected with plasmid expressing the rs4238001 or G2S SNP had −37% lower SR-BI protein expression compared with cells transfected with the wild-type SR-BI plasmid. The western blot is representative of two independent experiments. Panel C: SR-BI protein levels were significantly lower in carriers of the C allele (CC/TC) for the rs2278986 SNP compared to non-carriers (TT) (p=0.02, r=0.33, n=51).
Figure 4B:
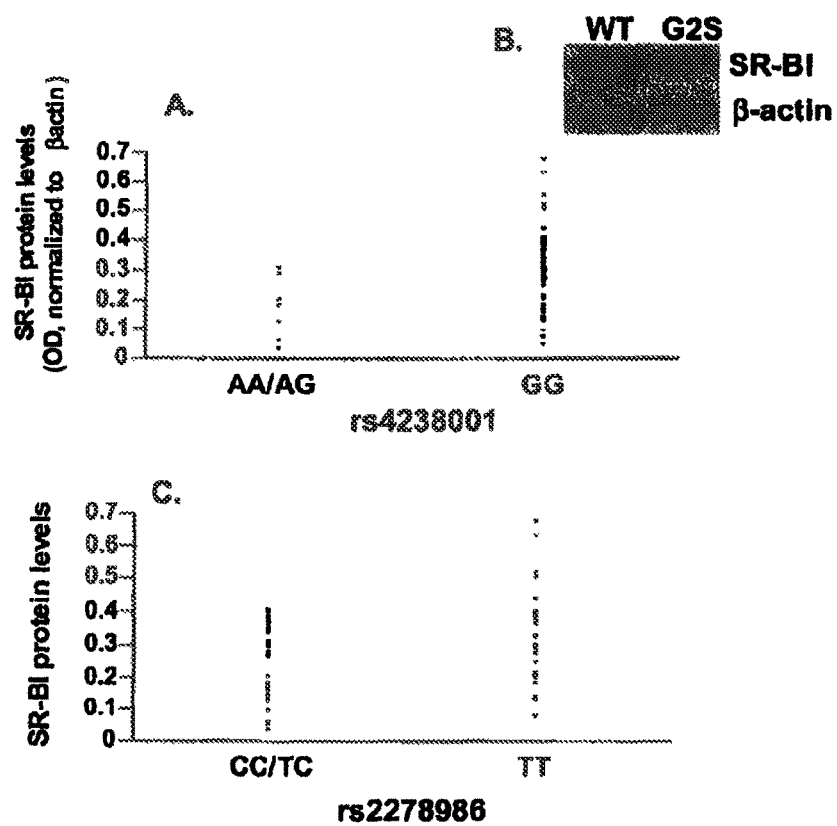
FIG. 4B. In female subjects, the association of macrophage SR-BI protein levels with the rs4238001 and rs2278986 SNPs. Panel A: SR-BI protein levels were significantly lower in carriers of the A allele (AA/AG) for the rs4238001 SNP compared with non-carriers (GG) (p=0.01, r=0.40, n=40). Panel B: COS-7 cells transiently transfected with plasmid expressing the rs4238001 or G2S SNP had ~0.37% lower SR-BI protein expression compared with cells transfected with the wild-type SR-BI plasmid. The western blot is representative of two independent experiments. Panel C: SR-BI protein levels were significantly lower in carriers of the C allele (CC/TC) for the rs2278986 SNP compared to non-carriers (TT) (p=0.02, r=0.40, n=36).

The association of SR-BI protein levels to each individual SNP shown in Table 4 were examined, and it was found that the subjects who were carriers of the minor A allele (AA/GA) for the rs4238001 SNP had significantly lower SR-BI protein levels (0.17±0.05, 47% lower) compared to non-carriers (0.32±0.02) (p=0.007, r=0.36, n=55) (FIG. 4A, Panel A, all subjects). The subjects who were carriers of the minor A allele (AA/GA) for the G2S SNP had significantly lower SR-BI protein levels (0.16±0.05, 48% lower) compared to non-carriers (0.31±0.02) (p=0.01, r=0.40, n=40) (FIG. 4B, Panel A, female subjects). Results of a sliding window haplotype analysis (data not shown) were also consistent with an association with low SR-BI levels driven by the G2S variant. Additionally, the single minor allele carrier for synonymous rs2070242 in exon 1 had a higher SR-BI level. COS-7 cells were transiently transfected with wild-type or G2S-SR-BI mutant plasmids. The results shown in FIG. 4A, Panel B and FIG. 4B, Panel B are representative of two independent experiments and showed that SR-BI protein levels were ~37% lower in cells transfected with the G2S construct compared to wild-type cells. The results in FIG. 4A, Panel C (all subjects) also showed that subjects who were carriers of the minor C allele (CC/TC) for the intron 3 rs2278986 SNP had significantly lower SR-BI protein levels (0.25±0.03, 26% lower) compared with subjects who were noncarriers (0.34±0.03) (p=0.02, r=0.33, n=51). FIG. 4B, Panel C (female subjects) also showed that subjects who were carriers of the minor C allele (CC/TC) for the intron 3 rs2278986 SNP had significantly lower SR-BI protein levels (0.25±0.02, 31% lower) compared with subjects who were noncarriers (0.36±0.03) (p=0.02, r=0.40, n=36).

In a multiple regression analysis using the same model as shown in Table 3A (all subjects), but including the rs4238001 and rs2278986 SNPs, each SNP was an independent predictor for SR-BI protein levels after adjustment for other covariates (p=0.02, data not shown). Linkage disequilibrium between the rs4238001 and rs2278986 SNPs were not observed.

Similarly, the covariates of BMI, HT use, CETP activity, LCAT activity, G2S SNP, rs2278986 [intron 3], and rs5888 [exon 8] polymorphisms were considered for female subjects, which together explained 42% of the variance in SR-BI protein levels (model p=0.04) (Table 3B). In a stepwise multiple regression analysis, BMI (p=0.05), G2S SNP (p=0.01), and rs2278986 [intron 3] (p=0.01) remained as significant independent predictors of SR-BI protein levels. Linkage disequilibrium between the rs4238001 (G2S SNP) and rs2278986 SNPs were not observed.

Example 6

Figure 5:
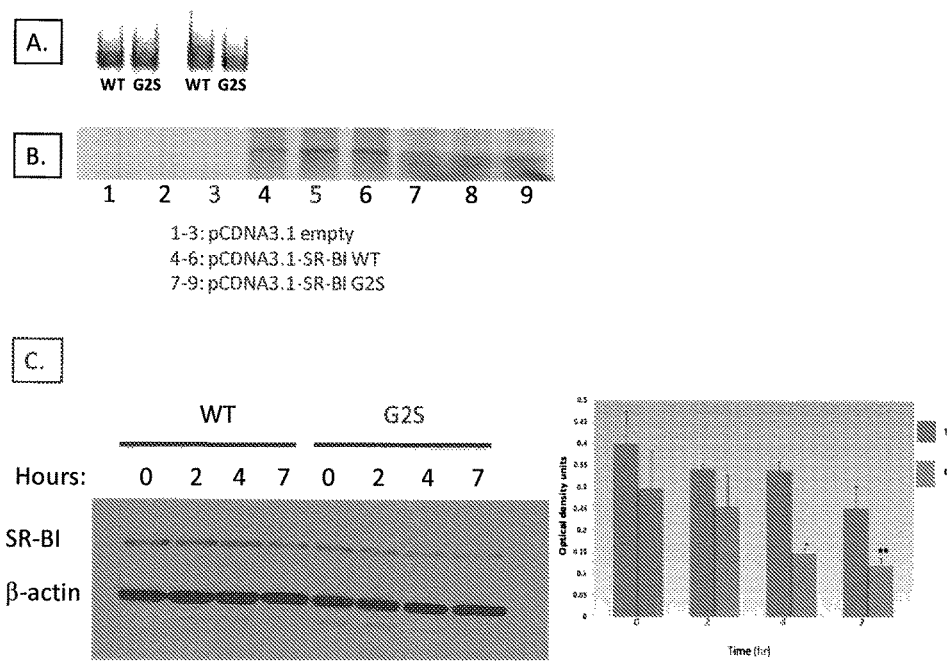
FIG. 5. The rs4238001 [G2S] variant is associated with alterations in SR-BI protein translation and degradation but not SR-BI mRNA transcription. Panel A: Transcription of SR-BI RNA was similar in rabbit reticulocytes transfected with plasmids expressing either SR-BI wild-type or GS2 variant. Panel B: Translation of SR-BI protein was reduced in rabbit reticulocytes transfected with plasmids expressing the G2S variant. Panel C: Stably expressing wild-type and G2S variant murine RAW macrophages were incubated with cycloheximide (140 µg/ml) for varying periods of time (0-7 h). SR-BI turnover was significantly greater in G2S cells by 4 h and 7 h as compared to wild-type cells (p<0.0007 and p<0.04, respectively).
Figure 6:
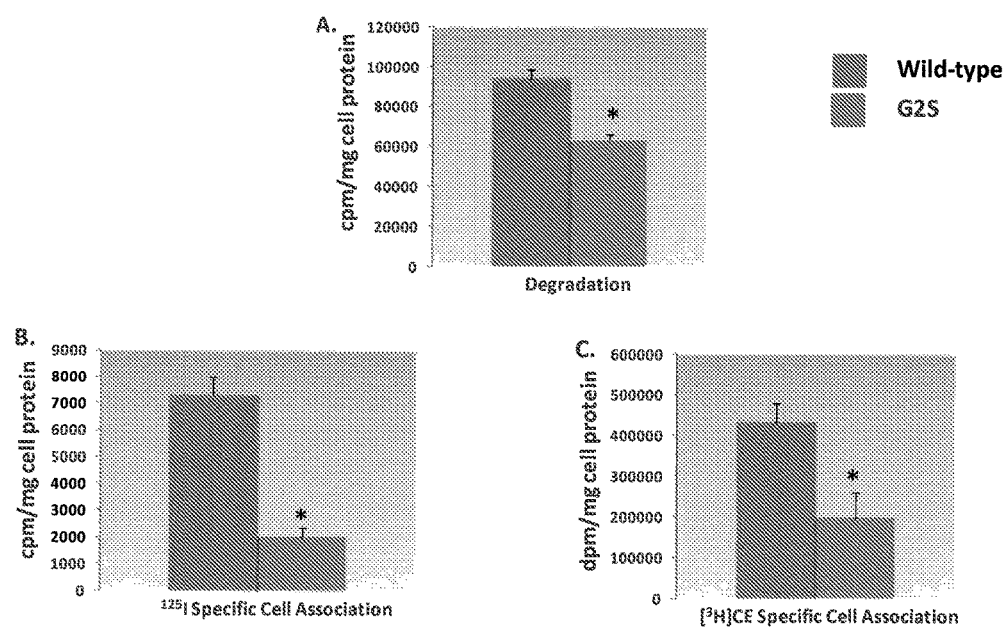
FIG. 6. Degradation and cell association of HDL is reduced in murine RAW macrophages stably expressing the SR-BI G2S variant. Panel A: Degradation of [$^{125}$I,$^3$H]-labeled HDL was significantly lower in G2S expressing cells (p<0.0004). Panel B: Specific and [$^3$H]CE cell association (panel C) were significantly lower in G2S expressing cells (p<0.0004).

In order to gain insight into the mechanism of how the G2S variant affected SR-BI protein expression, experiments were performed that measured SR-BI mRNA transcription, translation, protein degradation, and specific cell association of dual-radiolabeled HDL. As shown in FIG. 5A, there was no difference in the amount of mRNA transcribed in rabbit reticulocytes transfected with SR-BI wild-type or G2S variant. However, translation of SR-BI protein in the rabbit reticulocytes was lower in cells transfected with the G2S variant (FIG. 5B). SR-BI protein degradation in murine RAW macrophages that stably expressed wild-type or the G2S variant were next examined by incubating cells in the presence of cycloheximide for varying periods of time. As shown in FIG. 5C, by 4 h and 7 h the turnover of SR-BI protein was greater in cells expressing the G2S variant (p<0.0007 and p<0.04, respectively). Lastly, degradation and specific cell association of [125I,3H]-HDL in murine RAW macrophages was examined. As shown in FIG. 6, degradation and specific [125I] and [3H] cell association were significantly lower in cells expressing the G2S variant (p<0.0004).

Stronger associations have now bee shown between known SR-BI SNPs, SR-BI protein expression and HDL-C levels. Acton et al. (19 ARTERIOSCLER THROMB. VASC. BIOL. 1734-1743 (1999)) was first to show that a common SNP within exon 1, G2S, was significantly associated with higher HDL-C levels in men, suggesting that this SNP might be associated with lower SR-BI protein levels. The ex-vivo and in-vitro data shown in FIG. 4 provide strong support to this hypothesis. The frequency of this SNP in the HALP cohort was 12% and it contributed 13% of the variation in SR-BI protein levels, suggesting it is a relatively common SNP that exerts a major influence on SR-BI protein levels. In contrast to Acton et al. (19 ARTERIOSCLER THROMB. VASC. BIOL. 1734-1743 (1999)), in this HALP cohort the vast majority of the carriers with the minor A allele were women (5/7). In addition, the intron 3 SNP was identified as also having an independent effect on SR-BI protein levels.

TABLE 1A

Characteristics of the study population (n = 65).

| | |
|---|---|
| Age (years) | 57.2 ± 10.9 |
| Gender | |
| Men (%) | 14 (22) |
| Women (%) | 51 (78) |
| Race | |
| White (%) | 45 (69) |
| Black (%) | 17 (26) |
| Asian (%) | 2 (3) |
| Hispanic (%) | 1 (2) |
| Body mass index (kg/m$^2$) | 25.6 ± 5.7 |
| Total cholesterol (mmol/L) | 5.7 ± 0.9 |
| Triglycerides (mmol/L) | 0.88 ± .03 |
| HDL cholesterol (mmol/L) | 2.3 ± 0.5 |
| LDL cholesterol (mmol/L) | 3.0 ± 0.8 |

TABLE 1B

Characteristics of the study population stratified by gender (n = 65).

| | MEN | WOMEN |
|---|---|---|
| N = | 14 | 51 |
| Age (years) | 62.2 ± 11.7 | 55.7 ± 10.3* |
| Race | | |
| White (%) | 5 (36) | 40 (78)** |
| Black (%) | 7 (50) | 10 (20) |
| Asian (%) | 2 (14) | 0 (0) |
| Hispanic (%) | 0 (0) | 1 (2) |
| Body mass index (kg/m$^2$) | 25.2 ± 3.5 | 25.7 ± 6.0 |
| Total cholesterol (mmol/L) | 5.2 ± 0.98 | 5.8 ± 0.85$^+$ |
| Triglycerides (mmol/L) | 0.85 ± 0.34 | 0.88 ± 0.31 |
| HDL cholesterol (mmol/L) | 1.92 ± 0.28 | 2.36 ± 0.54** |
| LDL cholesterol (mmol/L) | 2.9 ± 0.96 | 3.0 ± 0.75 |
| Apolipoprotein A-I (mmol/L) | 1.53 ± 0.18 | 1.61 ± 0.17 |
| SR-BI protein (optical density) | 0.27 ± 0.12 | 0.30 ± 0.04 |

All p values compared to men:
*p = 0.03,
**p = 0.004,
$^+$p = 0.04

TABLE 2A

Multiple regression of independent predictors for HDL-C levels in all subjects.

| | |
|---|---|
| A. Initial full model (p < 0.0004, r = 0.72) | |
| Covariates: age (p = 0.89), gender (p = 0.005), BMI (p = 0.49), exercise (p = 0.15), alcohol use (p = 0.56), HT use (p = 0.67), TG (p = 0.02), hemoglobin A1C (p = 0.06), fish oil use (p = 0.007), smoking (p = 0.28), and SR-BI protein (p = 0.06). | |
| B. Final model (p < 0.0001, r = 0.70) | |
| 1. Gender | p = 0.001 |
| 2. A$_{1c}$ | p = 0.04 |
| 3. TG | p = 0.007 |
| 4. Fish oil use | p = 0.008 |
| 5. SR-BI | p = 0.01 |

TABLE 2B

Multiple regression of independent predictors for HDL-C levels in female subjects.

A. Initial full model (p < 0.001, r = 0.74)

Covariates: age (p = 0.48), BMI (p = 0.40), exercise (p = 0.09), alcohol use (p = 0.34), HT use (p = 0.55), TG (p = 0.05), hemoglobin A1C (p = 0.13), fish oil use (p = 0.008), smoking (p = 0.39), and SR-BI protein (p = 0.06).
B. Final model (p < 0.0002, r = 0.71)

| | |
|---|---|
| 1. TG | p = 0.01 |
| 2. exercise | p = 0.03 |
| 3. fish oil use | p = 0.01 |
| 5. SR-BI | p = 0.01 |

TABLE 3A

Multiple regression of independent predictors for SR-BI protein levels in all subjects.

A. Initial full model (p = 0.04, r = 0.65)

Covariates: gender (p = 0.03), BMI (p = 0.01), HT use (p = 0.25), ethnicity (p = 0.12), aspirin use (p = 0.70), CETP activity (p = 0.46), LCAT activity (p = 0.68), rs4238001 [G2S] (p = 0.07), rs2278986 [intron 3] (p = 0.05), and rs5888 [exon 8] (p = 0.65).
B. Final model (p = 0.001, r = 0.59)

| | |
|---|---|
| 1. BMI | p = 0.008 |
| 2. rs4238001 | p = 0.02 |
| 3. rs2278986 | p = 0.02 |

TABLE 3B

Multiple regression of independent predictors for SR-BI protein levels in female subjects.

A. Initial full model (p = 0.04, r = 0.65)

Covariates: BMI (p = 0.06), HT use (p = 0.36), CETP activity (p = 0.78), LCAT activity (p = 0.37), rs4238001 [G2S] (p = 0.05), rs2278986 [intron 3] (p = 0.04), and rs5888 [exon 8] (p = 0.50).
B. Final model (p = 0.004, r = 0.62)

| | |
|---|---|
| 1. BMI | p = 0.05 |
| 2. rs4238001 | p = 0.01 |
| 3. rs2278986 | p = 0.01 |

TABLE 4

Frequency of synonymous and nonsynonymous polymorphisms within SCARB1 gene.

| SNP name or genotype | Location within SCARB1 gene | Amino acid position change and Synonymous (S) or Nonsynonymous (NS) | Number of hyperalpha subjects who are either hetero- or homozygous for minor alleles | | |
|---|---|---|---|---|---|
| | | | 75th percentile (high SR-BI protein) | 50th percentile (intermediate SR-BI protein) | 25th percentile (low SR-BI protein) |
| Rs4238001 | Exon 1 | Gly→Ser | NS | 0 | 5 | 3 |
| Rs2070242 | Exon 1 | Ser→Ser | S | 1 | 0 | 0 |
| Rs10396208 | Exon 1 | Cys→Cys | S | 0 | 1 | 1 |
| Rs5891 | Exon 3 | Val→Iso | NS | 0 | 0 | 2 |
| Rs5889 | Exon 4 | Gly→Gly | S | 1 | 1 | 0 |
| Rs5892 | Exon 7 | Phe→Phe | S | 0 | 2 | 0 |
| Rs5888 | Exon 8 | Ala→Ala | S | 4 | 23 | 8 |
| G→A | Exon 10 | Gly→Arg 404 | NS | 0 | 0 | 1 |
| Rs1069261 | Intron 1 | Insertion TG | | 6 | 22 | 8 |
| Rs2278986 | Intron 3 | — | — | 1 | 20 | 8 |
| Rs5801571 | Intron 9 | Deletion C | | 4 | 4 | 2 |
| Rs838897 | Intron 10 | — | — | 4 | 8 | 2 |

What is claimed is:

1. A method comprising the steps of (a) detecting the presence of the A allele of rs4238001 in a biological sample from a human subject using a microarray; and (b) administering a statin, aspirin, and/or anti-platelet agent to the human subject.

2. The method of claim 1, wherein said subject has hyperalphalipoproteinemia.

3. The method of claim 1, wherein said subject is a female.

* * * * *